(12) United States Patent
Brightbill

(10) Patent No.: US 7,083,822 B2
(45) Date of Patent: Aug. 1, 2006

(54) OVERLAPPING COATED STENTS

(75) Inventor: Jerry Brightbill, Newton, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 10/133,182

(22) Filed: Apr. 26, 2002

(65) Prior Publication Data

US 2003/0204245 A1 Oct. 30, 2003

(51) Int. Cl.
*A61F 2/06* (2006.01)

(52) U.S. Cl. .................... 427/2.25; 623/1.42; 623/1.34

(58) Field of Classification Search ............... 623/1.42, 623/1.1, 1.44, 1.27, 1.46, 1.34, 1.16; 427/2.25, 427/230–239, 256–288
See application file for complete search history.

(56) References Cited

U.S. PATENT DOCUMENTS

| | | | |
|---|---|---|---|
| 4,739,762 A | | 4/1988 | Palmaz |
| 5,064,435 A * | 11/1991 | Porter ........................ 623/23.7 |
| 5,133,732 A | | 7/1992 | Wiktor |
| 5,292,331 A | | 3/1994 | Boneau |
| 5,421,955 A | | 6/1995 | Lau et al. |
| 5,824,043 A * | 10/1998 | Cottone, Jr. ............... 623/1.13 |
| 5,824,049 A * | 10/1998 | Ragheb et al. ............. 623/1.44 |
| 5,873,904 A * | 2/1999 | Ragheb et al. ............. 623/1.13 |
| 5,916,264 A * | 6/1999 | Von Oepen et al. ........ 623/1.15 |
| 6,090,127 A | | 7/2000 | Globerman |
| 6,120,535 A * | 9/2000 | McDonald et al. ......... 623/1.39 |
| 6,174,329 B1 * | 1/2001 | Callol et al. ............... 623/1.34 |
| 6,251,136 B1 * | 6/2001 | Guruwaiya et al. ........ 623/1.46 |
| 6,284,305 B1 * | 9/2001 | Ding et al. ................. 427/2.28 |
| 6,334,871 B1 | | 1/2002 | Dor et al. |
| 6,395,326 B1 * | 5/2002 | Castro et al. ............... 427/2.24 |
| 6,451,373 B1 * | 9/2002 | Hossainy et al. ........... 427/2.25 |
| 6,506,437 B1 * | 1/2003 | Harish et al. ............... 427/2.25 |
| 6,652,575 B1 * | 11/2003 | Wang ......................... 623/1.15 |
| 2003/0003220 A1 * | 1/2003 | Zhong et al. ................. 427/2.1 |
| 2003/0083646 A1 * | 5/2003 | Sirhan et al. ............. 604/891.1 |
| 2003/0105511 A1 * | 6/2003 | Welsh et al. ................ 623/1.15 |

FOREIGN PATENT DOCUMENTS

WO  WO 99/56663  * 11/1999

* cited by examiner

*Primary Examiner*—Paul B. Prebilic

(57) ABSTRACT

The present invention avoids a patient receiving a double dose of a therapeutic agent when a coated stent is overlapped with another coated stent within a vessel. A stent having a therapeutic coating on a portion of the stent is delivered within a vessel such that the portion of the stent not having a therapeutic coating is inserted within or overlaps a second coated stent. A radiopaque marker on the stent or delivery catheter guides positioning of the stent such that there is minimal or no overlap of the therapeutic coatings on the two stents.

7 Claims, 7 Drawing Sheets

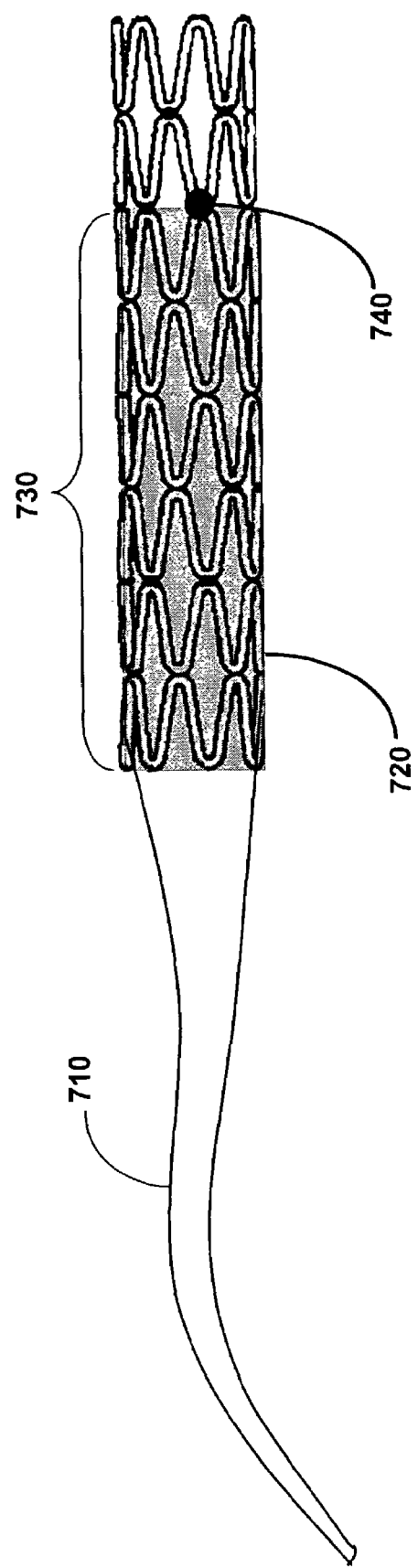

OVERLAPPING COATED STENTS

TECHNICAL FIELD

This invention relates generally to biomedical stents. More specifically, the invention relates to coated stents that are designed to be overlapped when delivered within a vessel.

BACKGROUND OF THE INVENTION

Stents are generally cylindrical shaped devices that are radially expandable to hold open a segment of a vessel or other anatomical lumen after implantation into the body lumen. Stents have been developed with coatings to deliver drugs or other therapeutic agents.

Various types of stents are in use, including expandable and self-expanding stents. Expandable stents generally are conveyed to the area to be treated on balloon catheters or other expandable devices. For insertion, the stent is positioned in a compressed configuration along the delivery device, for example crimped onto a balloon that is folded or otherwise wrapped about a guide wire that is part of the delivery device. After the stent is positioned across the lesion, it is expanded by the delivery device, causing the length of the stent to contract and the diameter to expand. For a self-expanding stent, commonly a sheath is retracted, allowing expansion of the stent.

Stents are used in conjunction with balloon catheters in a variety of medical therapeutic applications including intravascular angioplasty. For example, a balloon catheter device is inflated during PTCA (percutaneous transluminal coronary angioplasty) to dilate a stenotic blood vessel. The stenosis may be the result of a lesion such as a plaque or thrombus. After inflation, the pressurized balloon exerts a compressive force on the lesion, thereby increasing the inner diameter of the affected vessel. The increased interior vessel diameter facilitates improved blood flow. Soon after the procedure, however, a significant proportion of treated vessels re-narrow.

To prevent restenosis, short flexible cylinders, or stents, constructed of metal or various polymers, are implanted within the vessel to maintain lumen size. The stents acts as a scaffold to support the lumen in an open position. Various configurations of stents include a cylindrical tube defined by a mesh, interconnected stents or like segments. Some exemplary stents are disclosed in U.S. Pat. No. 5,292,331 to Boneau, U.S. Pat. No. 6,090,127 to Globerman, U.S. Pat. No. 5,133,732 to Wiktor, U.S. Pat. No. 4,739,762 to Palmaz and U.S. Pat. No. 5,421,955 to Lau.

Stent insertion, however, may cause undesirable reactions such as inflammation, infection, thrombosis, and proliferation of cell growth that occludes the passageway. One approach to minimize these undesirable reactions has been to provide the stents with an ability to deliver one or more therapeutic agents. Coated stents, for example, may have coatings to deliver drugs or other therapeutic agents at the site of the stent that may assist in preventing these conditions. The coatings must be bioengineered to control the release of highly potent and potentially toxic drugs. Besides coating the stent to provide the stents with an ability to deliver one or more therapeutic agents, other approaches may also be used, such as sheath wrapped stents (such as those depicted in Froix, U.S. Pat. No. 6,019,789) as well as other delivery matrices (such as those depicted in Kaplan, U.S. Pat. No. 5,342,348).

When extending an area of treatment beyond the length of an individual coated stent, a second coated stent may be positioned at least partially within a previously delivered coated stent, resulting in an overlap of the coatings. Assuming each coating is used to deliver a therapeutic agent, then the area of overlap may receive a double dose of the therapeutic agent. This over dosing may cause undesirable side effects to the artery and potentially grave consequences for the patient. Therefore, it would be desirable to have a stent system which delivers one or more therapeutic agents through coatings or other approaches but which avoids the possibility of overdosing in the area of stent overlap.

SUMMARY OF THE INVENTION

One aspect of the present invention is a stent having a therapeutic coating on a portion of the stent. The stent may also have at least one radiopaque marker.

Another aspect of the present invention is a stent having a therapeutic coating on at least a portion of the stent and a non-therapeutic coating on a portion of the stent. The stent may also have at least one radiopaque marker.

A further aspect of the present invention is a stent having a therapeutic coating, wherein the coating is removable with a solvent. The stent also has a plurality of radiopaque markers.

Another aspect of the present invention is a system comprising a first stent coated with a first coating and a second stent having at least a first portion and a second portion, the second portion coated with a second coating. The second stent may also have a radiopaque marker for positioning the second stent within the vessel and relative to the first stent.

A further aspect of the present invention is a method of delivering overlapping stents in a vessel. A first stent, including a therapeutic coating disposed on at least a portion of the exterior surface of the stent framework and also including one of a visible endpoint or a radiopaque marker, is delivered and expanded. A second stent, including a therapeutic coating disposed on at least a portion of the exterior surface of the stent framework and also including one of a visible endpoint or a radiopaque marker, is delivered. The second stent is positioned based on the visible endpoint or radiopaque marker of the first stent and the visible endpoint or radiopaque marker of the second stent such that there is minimal or no overlap of therapeutic coatings of the first and second stents. The second stent is expanded.

Another aspect of the present invention is a method of manufacturing a coated stent designed for insertion into another stent. A stent is provided, and a therapeutic coating is applied to at least a portion of an exterior surface of the stent. The therapeutic coating may be removed from a portion of the exterior surface of the stent, or a portion of an exterior surface of the stent may be masked prior to applying the therapeutic coating. The masking material may be removed from the exterior surface of the stent after the coating is applied. At least one radiopaque marker may be applied.

Yet another aspect of the present invention is a stent delivery system, comprising a catheter, a stent coupled to the catheter, a therapeutic coating on at least a portion of the stent, and a radiopaque marker on one of the catheter or the stent.

The aforementioned, and other features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims and equivalents thereof.

BRIEF DESCRIPTION OF THE DRAWINGS

FIG. 7 is an illustration of one embodiment of a stent delivery system, in accordance with the present invention.

DETAILED DESCRIPTION OF THE PRESENTLY PREFERRED EMBODIMENTS

Figure 1:
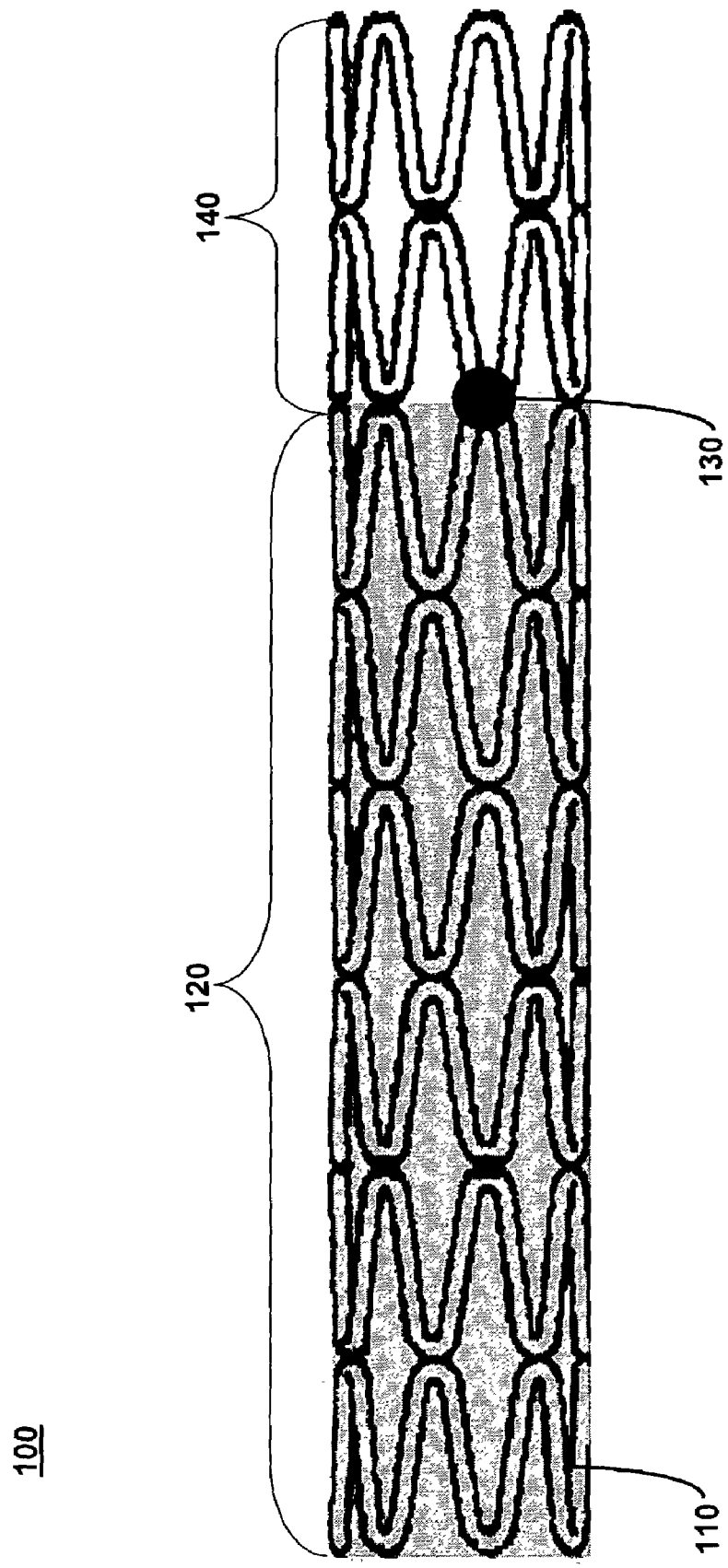
FIG. 1 is an illustration of one embodiment of a stent designed for insertion into another stent, in accordance with the present invention.

One aspect of the present invention is a stent designed for insertion into another stent. One embodiment of the stent, in accordance with the present invention, is illustrated in FIG. 1 at 100. Stent 100 includes a stent framework 110, a therapeutic coating 120, and a radiopaque marker 130. For clarity, it must be set forth that while the coating 120 is depicted as a shaded region of the entire portion of the stent 100 (in this FIG. as well as in all the other FIGS. of this application), in the preferred embodiment the coating covers only the stent framework and does not also cover the openings or cells there between. Of course, however, the invention should not be read as being limited to only stents having a coated framework per se, i.e. having an open, uncovered cells. The invention may also be used on stents featuring a drug delivery vehicle in which the cells are not open, including sheath wrapped stents (such as those depicted in Froix, U.S. Pat. No. 6,019,789) as well as other delivery matrices (such as those depicted in Kaplan, U.S. Pat. No. 5,342,348). In such embodiments the sheath or other delivery matrices would be disposed on only a portion of the length of the stent.

Stent framework 110 may be made of a wide variety of medical implantable materials, such as stainless steel, nitinol, tantalum, ceramic, nickel, titanium, aluminum, polymeric materials, tantalum, MP35N, stainless steel, titanium ASTM F63-83 Grade 1, niobium, high carat gold K 19–22, polymers or combinations of the above.

Therapeutic coating 120 includes one or more therapeutic agent(s) such as an antineoplastic agent, an antiproliferative agent, an antibiotic, an anti-inflammatory agent, combinations of the above, and the like. The coating may be a polymer, including, but not limited to, urethane, polycaprolactone (PCL), polymethylmethacrylate (PMMA), combinations of the above, and the like.

Stent portion 140 may carry no coating, having been masked prior to application of the therapeutic coating or having been held out of the coating material. Stent portion 140 may also carry a non-therapeutic coating that has been applied, for example, directly to the stent framework or over a therapeutic coating. This non-therapeutic coating may be a protective coating material such as polymers generally or parylene or phosphorylcholine or silanes.

Radiopaque marker 130 is shown applied at the point where therapeutic coating 120 ends. However, radiopaque marker 130 could be applied anywhere on the stent (having a fixed distance from the demarcation between the therapeutic coating 120 and the remaining stent portion 140) or could even be carried on the catheter used to deliver stent 100. The radiopaque marker is used to guide insertion of stent 100 into a second stent within a vessel such that there is minimal or no overlap of therapeutic coatings on both stents. In such a manner the present invention makes possible the usage of coated stents without over-dosing a region of the artery.

Figure 2:
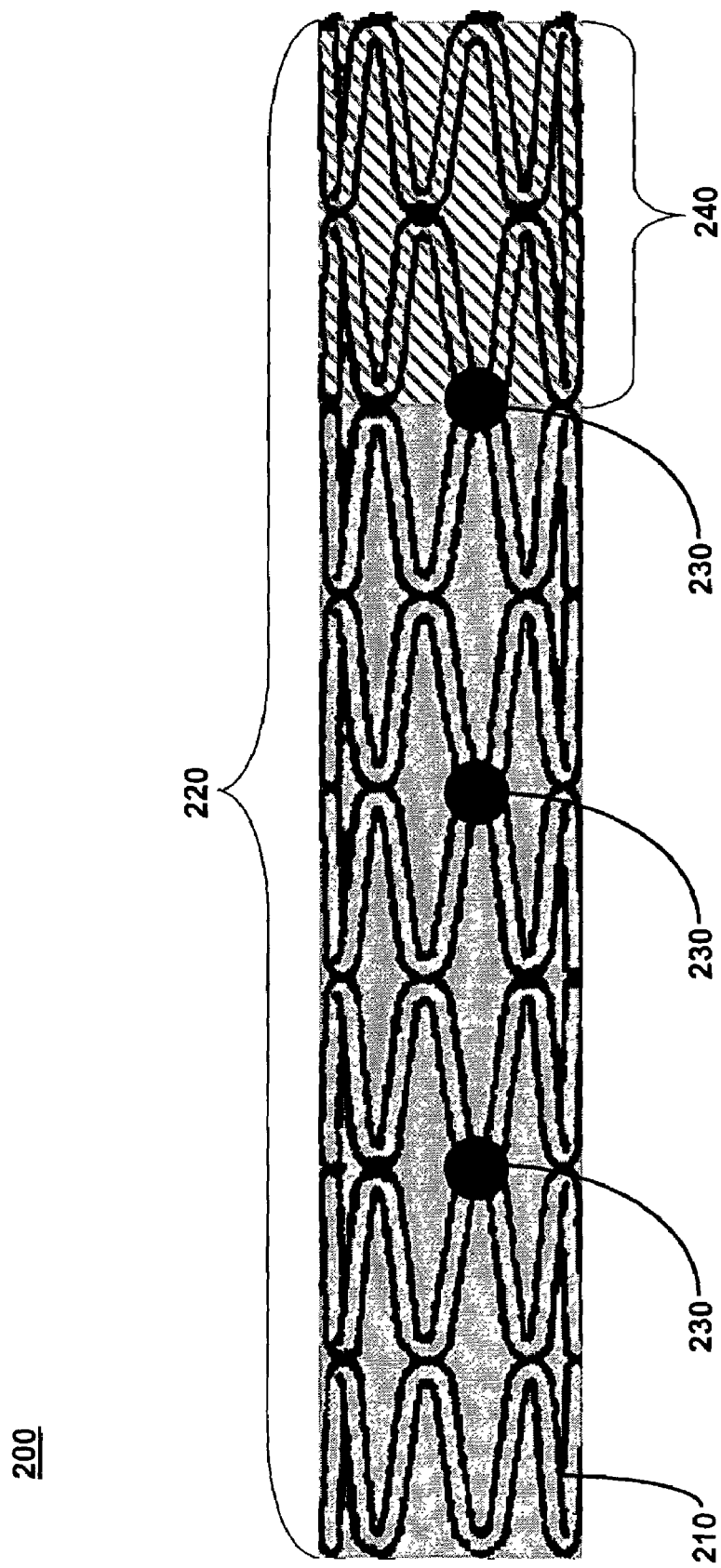
FIG. 2 is an illustration of another embodiment of a stent designed for insertion into another stent, in accordance with the present invention.

Another embodiment of the stent, in accordance with the present invention, is illustrated in FIG. 2 at 200. Stent 200 includes a stent framework 210, a therapeutic coating 220, and multiple radiopaque markers 230.

Stent framework 210 may be made of a wide variety of medical implantable materials, such as those already discussed above.

Therapeutic coating 220 includes one or more therapeutic agent(s) such as an antineoplastic agent, an antiproliferative agent, an antibiotic, an anti-inflammatory agent, combinations of the above, and the like. The coating may be a polymer, including, but not limited to, urethane, polycaprolactone (PCL), polymethylmethacrylate (PMMA), combinations of the above, and the like.

Radiopaque markers 230 are shown applied at three evenly spaced points along the length of the stent. However, radiopaque markers 230 could be applied at any number of points along stent 200.

A solvent is used to remove therapeutic coating 220 from a portion 240 of stent 200, up to a point indicated by a radiopaque marker. Suitable solvents that may be used include, but are not limited to, acetone, ethyl acetate, tetrahydrofuran (THF), chloroform, N-methylpyrrolidone (NMP), combinations of the above, and the like. The appropriate radiopaque marker 230 that indicates the end of the therapeutic coating is then used to guide insertion of stent 200 into a second stent within a vessel such that there is minimal or no overlap of coatings on both stents.

The present embodiment is not limited to a particular radiopaque stent marker. One example of a radiopaque stent marker particularly useful in a tubular slotted stent is described in U.S. Pat. No. 6,334,871 B1, incorporated herein by reference.

Figure 3:
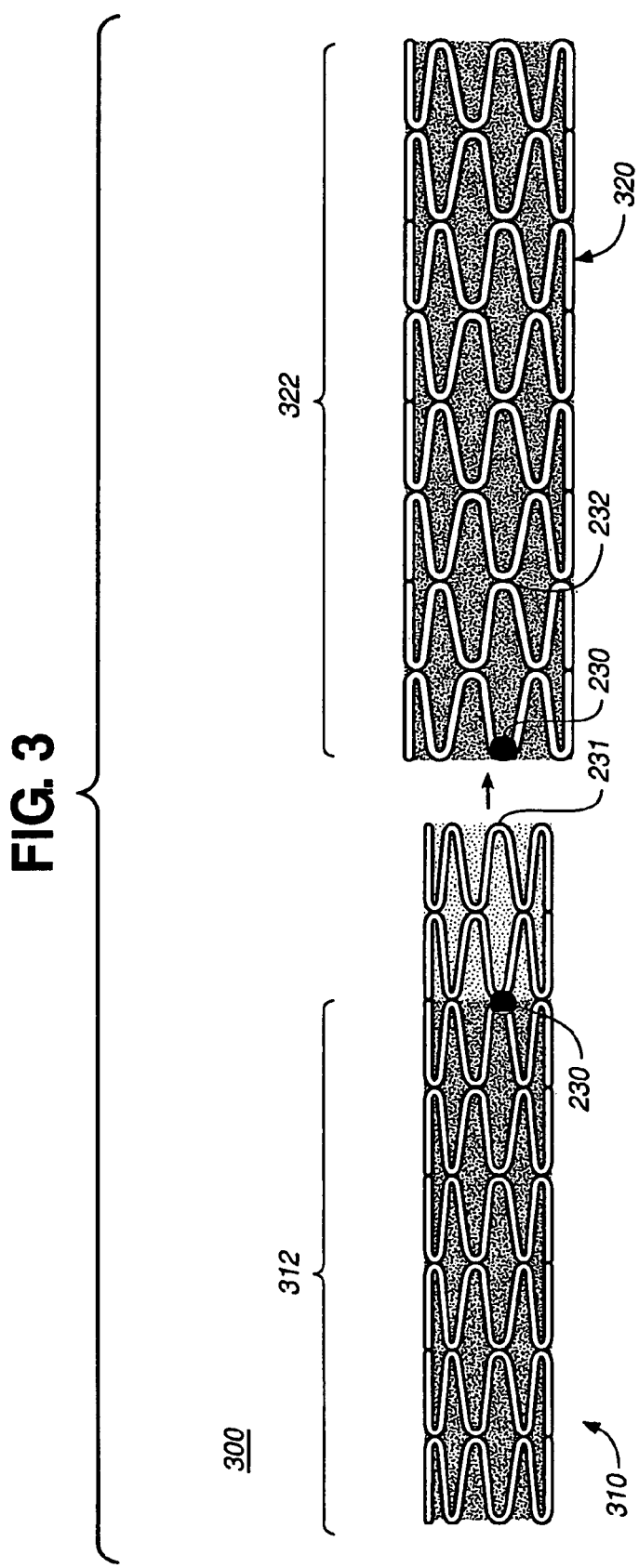
FIG. 3 is an illustration of one embodiment of a system for treating a vessel, in accordance with the present invention.

Another aspect of the present invention is a system for treating a vessel. One embodiment of the system, in accordance with the present invention, is illustrated in FIG. 3 at 300. System 300 includes a first stent 310 and a second stent 320. Stent 310 is partially coated with a therapeutic coating 312. Stent 320 is coated with a therapeutic coating 322. Stents 310 and 320 include radiopaque markers 230.

Stent 320 has been delivered and expanded within a vessel. Stent 310 is being delivered within the same vessel. The radiopaque marker on stent 310 may be aligned with the edge of stent 320 to position stent 310 partially within stent 320 such that there is minimal or no overlap of the therapeutic coatings on both stents. Alternatively, if the end of stent 320 is visible, stent 310 may be positioned partially within stent 320 based on the radiopaque marker 230 of stent 310 and the visible end of stent 320 with no need for a radiopaque marker on stent 320. Radiopaque markets 230 could also be applied at other points on stents 310 and 320, for example, at the points identified as 231 and 232, and used to correctly position stent 310 partially within stent 320 such that there is minimal or no overlap of the therapeutic coatings on both stents. In such a manner the present invention makes possible the usage of coated stents without over-dosing a region of the artery.

Figure 4:
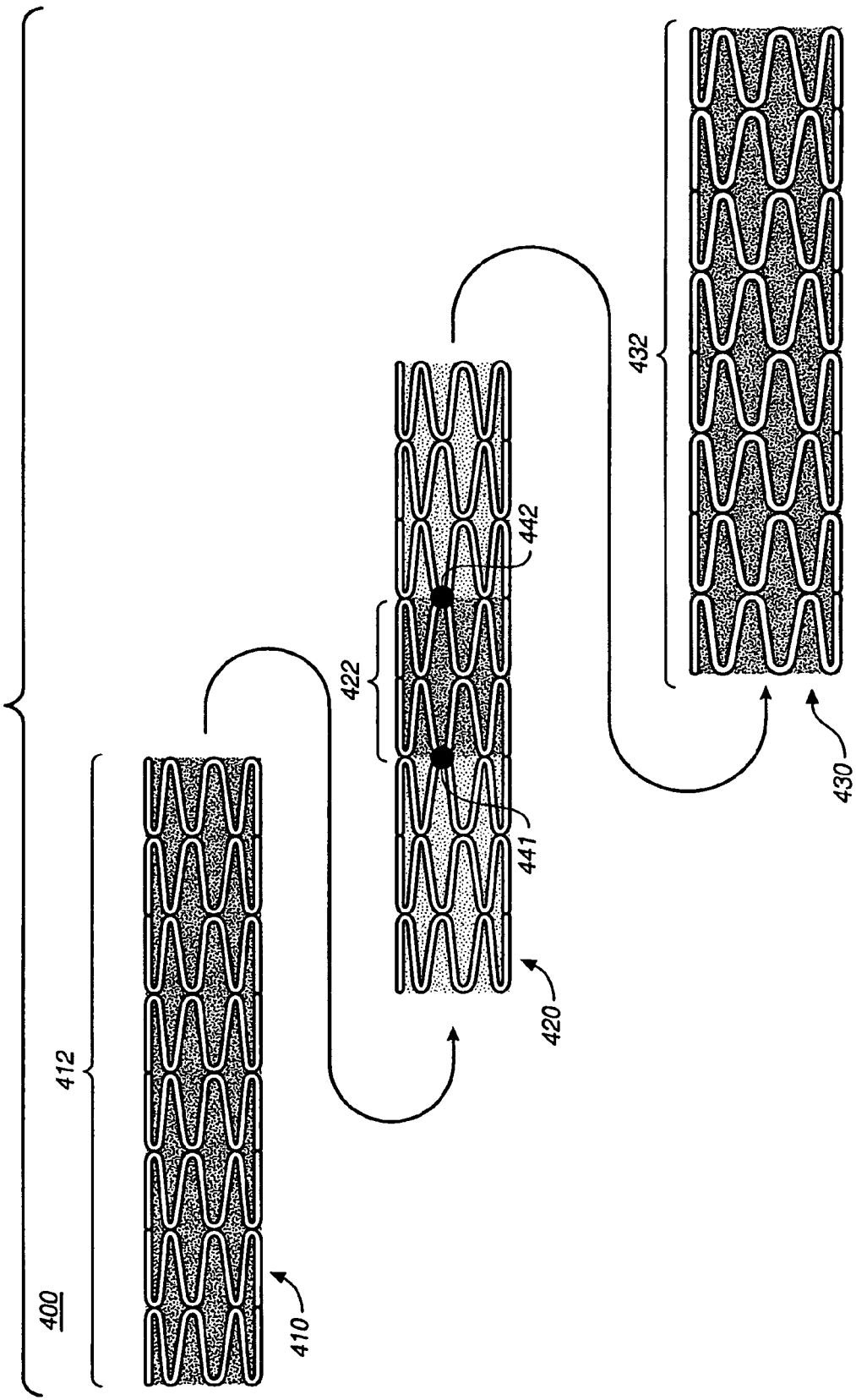
FIG. 4 is an illustration of another embodiment of a system for treating a vessel, in accordance with the present invention.

Another embodiment of the system, in accordance with the present invention, is illustrated in FIG. 4 at 400. System 400 includes a first stent 410, a second stent 420, and a third stent 430.

Stent 430 has been delivered and expanded within a vessel. Stent 420 is being delivered within the same vessel. After stent 420 has been delivered and expanded, stent 410 will then be delivered and expanded. Stent 410 is coated with a therapeutic coating 412. Stent 420 is partially coated with a therapeutic coating 422. Stent 430 is coated with a therapeutic coating 432. Stent 420 includes radiopaque markers 441 and 442.

Radiopaque marker 442 on stent 420 is aligned with the end point of stent 430 to position stent 420 partially within stent 430 such that there is minimal or no overlap of the therapeutic coatings on both of these stents. After stent 420 has been positioned and expanded, the end point of stent 410 is aligned with radiopaque marker 441 on stent 420 to position stent 410 partially within stent 420 such that there is minimal or no overlap of the therapeutic coatings on both of these stents and thus over-dosing of the artery in the region of the artery is avoided.

Figure 5:
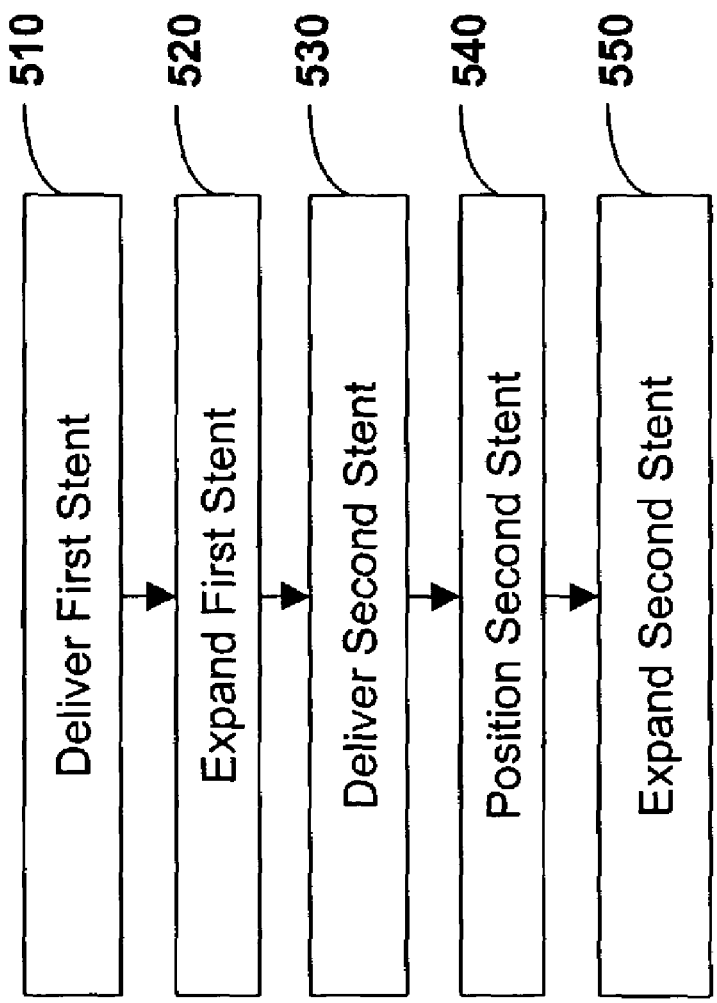
FIG. 5 is a flow diagram of one embodiment of a method of delivering overlapping stents in a vessel, in accordance with the present invention.

Yet another aspect of the present invention is a method of delivering overlapping stents in a vessel. FIG. 5 shows a flow diagram of one embodiment of a method of delivering overlapping stents in a vessel, in accordance with the present invention at 500.

A first stent is delivered within a vessel (Block 510). This first stent has a therapeutic coating disposed on the exterior surface of the stent framework. The first stent is expanded (Block 520). A second stent is delivered within the same vessel (Block 530). This second stent has a therapeutic coating disposed on a portion of the exterior surface of the stent framework. The second stent is positioned partially within the first stent, based on the visible endpoint of the first stent and a radiopaque marker on the second stent (Block 540). The second stent is expanded (Block 550).

Figure 6:
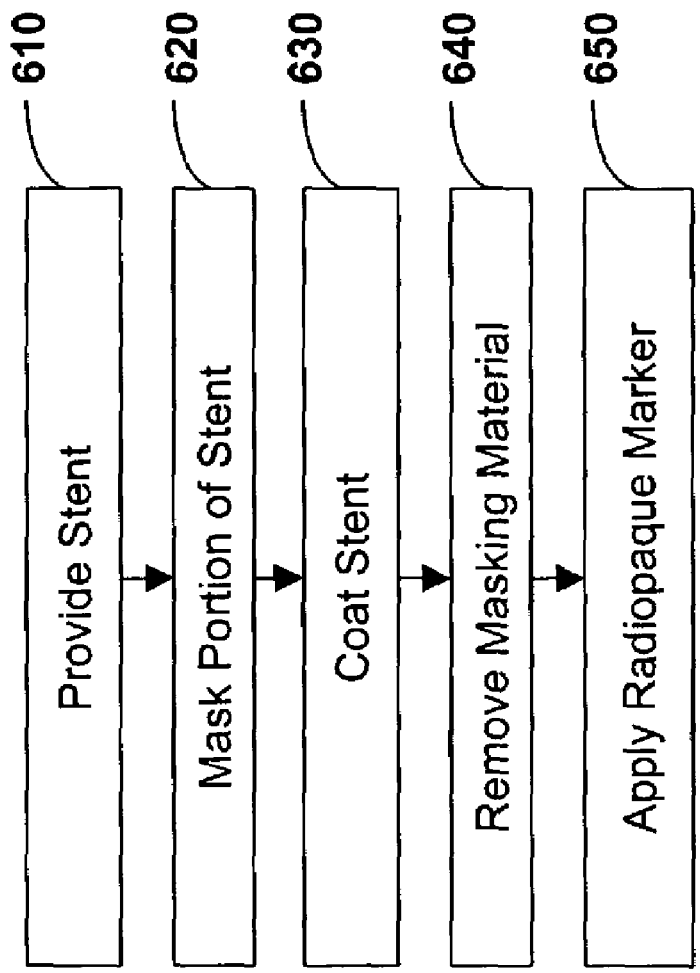
FIG. 6 is a flow diagram of one embodiment of a method of manufacturing a coated stent designed for insertion into another stent, in accordance with the present invention.

A further aspect of the present invention is a method of manufacturing a coated stent designed for insertion into another stent. FIG. 6 shows a flow diagram of one embodiment of a method of manufacturing a coated stent designed for insertion into another stent, in accordance with the present invention at 600.

A stent is provided (Block 610). A portion of the exterior surface of the stent is masked using an adhesive-backed material (Block 620). A therapeutic coating is sprayed onto the exterior surface of the stent (Block 630). The adhesive-backed masking material is removed (Block 640). A radiopaque marker is applied to the stent (Block 650).

Still another aspect of the present invention is a stent delivery system including a catheter, a stent coupled to the catheter, a therapeutic coating on at least a portion of the stent, and a radiopaque marker. FIG. 7 shows an illustration of a stent delivery system, in accordance with the present invention at 700.

Catheter 710 may include a balloon used to expand stent 720, or it may include a sheath that retracts to allow expansion of a self-expanding stent. Both types of catheter are well known in the art.

Stent 720 may include a framework consisting of, for example, 316L stainless steel. Therapeutic coating 730 is shown distributed over a portion of the stent. Radiopaque marker 740 may be carried on either the catheter or the stent. Radiopaque marker 740 guides insertion of the stent into a second stent within a vessel such that there is minimal or no overlap of therapeutic coatings on both stents. In such a manner the present invention makes possible the usage of coated stents without over-dosing a region of the artery.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

What is claimed is:

1. A method of manufacturing a stent having a therapeutic coating, said stent designed for insertion into another stent having a therapeutic coating such that there is minimal or no overlap of therapeutic coatings on both stents, comprising:
   providing a stent;
   applying a therapeutic coating to a continuous portion of the exterior surface of
   the stent, while excluding said coating from a continuous end portion of the exterior surface of said stent such that the continuous end portion is left uncoated; and
   applying at least one radiopaque marker as a point application where the therapeutic coating disposed on the exterior surface meets the uncoated end portion of the exterior surface.

2. The method of claim 1 further comprising masking said continuous end portion of the exterior surface of the stent with a masking material prior to applying said therapeutic coating.

3. The method of claim 2 wherein the masking material is a protective polymer coating material.

4. The method of claim 3 wherein the protective polymer coating material is parylene.

5. The method of claim 2 further comprising:
   removing said masking material from the stent after the therapeutic coating is applied.

6. The method of claim 5 wherein the stent is masked by one or more materials selected from the group consisting of an adhesive-backed material, a tube that encapsulates a portion of the stent and a removable coating.

7. A method of manufacturing a stent having a therapeutic coating, said stent designed for insertion into another stent having a therapeutic coating such that there is minimal or no overlap of therapeutic coatings on both stents, comprising:
   providing a stent;
   applying a therapeutic coating to a continuous portion of the exterior surface of the stent;
   removing the therapeutic coating from a continuous end portion of the exterior surface of the stent using a solvent such that the continuous end portion becomes uncoated; and
   applying at least one radiopaque marker as a point application where the therapeutic coating disposed on the exterior surface meets the uncoated end portion of the exterior surface to assist in the placement of said stent into said another stent to minimize overlap of therapeutic coatings on both stents.

* * * * *